United States Patent [19]

Theodore et al.

[11] Patent Number: 5,716,959
[45] Date of Patent: Feb. 10, 1998

[54] METHOD OF TREATING DISEASE WITH PIPERAZINE ZWITTERION COMPOUNDS

[75] Inventors: T. Ronald Theodore, P.O. Box 513, Forestdale, Mass. 02644; Roscoe L. Van Zandt, Arlington, Tex.

[73] Assignee: T. Ronald Theodore, Forestdale, Mass.

[21] Appl. No.: 600,901

[22] Filed: Feb. 13, 1996

[51] Int. Cl.$^6$ .................. A61K 31/395; A61K 31/685
[52] U.S. Cl. .............. 514/255; 424/531; 514/76; 514/77; 514/564
[58] Field of Search ................ 514/76, 77, 255, 514/564; 424/531

[56] References Cited

U.S. PATENT DOCUMENTS 4,753,942  6/1988  O'Sullivan et al. .................. 514/255

OTHER PUBLICATIONS

Synzynys et al., Chemical Abstracts, vol. 102, abstract 20432, 1985.

"Effects of In-vivo Administration of Taurine and HEPES on the Inflammatory Response in Rats" *Pharmacy and Pharmacology*, vol. 46, No. 9, Sep. 1994.

Norman E. Good et al, Hydrogen Ion Buffers for Biological Research, Feb. 1966, vol. 5, No. 2, *Biochemistry*.

*The Merck Index*, 12th Edition, Apr. 1996.

*Primary Examiner*—Richard L. Raymond
*Attorney, Agent, or Firm*—Richard P. Crowley

[57] ABSTRACT

A substituted piperazine zwitterion composition containing, for example, as an active ingredient, HEPES (N-2 Hydroxyethylpiperazine-N'-2 Ethane Sulfonic Acid), and method useful for treatment of cancer, autoimmune, arthritis and other mammalian diseases.

14 Claims, No Drawings

METHOD OF TREATING DISEASE WITH PIPERAZINE ZWITTERION COMPOUNDS

BACKGROUND OF THE INVENTION

In the world population, the incidence of cancer is very significant. It is estimated that one in four persons will develop cancer sometime in their life. Half of all persons who develop cancer will die from it. The incidence of cancer-related deaths has been doubling every thirty years in the United States. There are many factors associated with the increasing incidence of disease. Many people live longer, and the incidence may increase due to an aging population. Environmental toxins and/or genetic changes may also play a role in the increase.

There has also been an increase in the incidence of infectious diseases, particularly viral infections. Many virulent strains are now seen. Virally-mediated infections, such as hepatitis (A, B and C) and HIV-type infections have had a significant impact on the population. Some cancers, such as Kaposi's sarcoma, are associated with viral infections.

There are many diseases associated with autoimmune disorders. Rheumatoid arthritis and myasthenia gravis are examples. The etiology of many autoimmune diseases is not clear. Genetic and/or environmental aspects may contribute in several ways to alter hemopoietic and immune responses. Certain drugs may trigger autoimmune responses as well as induce immunosuppressed states.

There are four basic approaches to the treatment of cancer. These approaches are sometimes combined in the form of multimodality therapies. The basic approaches are surgical resection, chemotherapy, radiation and immunotherapy. Alternative approaches include naturopathy, herbal treatments and acupuncture.

Therapies for autoimmune disease have been limited. Primarily, the use of steroids has been a mainstay. Advanced cases of diseases, such as rheumatoid arthritis and myasthenia gravis, rarely respond well.

Infectious disease therapies have had many advances with the use of antibiotics. There have been a few antiviral compounds developed. Their use is fairly limited to a few types of infection. HIV is yet to respond to any significant therapy. Immune therapies have had limited success in hepatitis.

Over the last fifty years, there has been a slow development of various immunotherapies. These have included the use of specific cytokines, chemokines, lymphokines and other immunological substances derived from cell culture research and cloned. In the past, it has been shown that certain fractions of cell cultures have produced specialized responses in tumors. Chemotherapeutic agents and radiation have generated some tumor responses, but have high toxicity.

The need for developing agents and compositions that effectively treat cancer, cancer pain, immunologically-mediated diseases and certain infectious diseases continues to be very important.

SUMMARY OF THE INVENTION

The present invention relates to a method for the treatment of diseases in mammals by the administration of zwitterionic compositions as safe and effective biological response modifiers to the mammals and to the zwitterionic compositions used and the preparation of such zwitterionic compositions for use in treatment.

The present invention demonstrates that zwitterionic molecules have a definitive effect as a biological response modifier (BRM). Zwitterionic molecules are substances that have neither a negative nor a positive charge. Zwitterions are compounds having a net charge on the molecule which is zero and which have positive and negative groups that are equally ionized in the molecule, and are dipolar molecules containing, for example, hydroxy groups and also acid groups, like carboxylic or sulfonic acid groups.

One zwitterion compound useful in the invention, alone or with other compounds, zwitterion compounds or as other active ingredients or cell cultures in a therapeutic amount, comprises inhibited piperazine zwitterionic compounds, such as, but not limited to, an N-2 hydroxyl or amino alkyl piperazine-N-2alkane acid, like carboxylic acid, phosphoric or sulfonic acid and its effective, non-toxic salts and derivatives and substituents. In particular, the invention is directed to the use of, and is particularly effective with, a zwitterion known as HEPES and its acid salts; e.g. sodium or potassium, known as N-2Hydroxyethylpiperazine-N'-2 Ethane Sulfonic Acid, formula weight 238 (i.e. $C_2H_{16}N_2O_4S$) (HEPES). They have routinely been used in cell cultures as a buffer and, to date, were not suspected to have any effects on cells, physiologic pathways or disease processes.

It is now shown that HEPES and other zwitterionic compounds are true biological response modifiers (BRM). They effect positive changes in cancer, cancer pain, autoimmune disease and viral infections. They can be used alone and/or in combination with mammalian serum and/or in combination with cell culture supernatants utilizing mammalian serum. There appears to be a possible interaction with serum and/or cell culture supernatants. The bioactive pathways may be affected by various compositions of zwitterionic molecules. It remains clear that they can play a role as a biological response modifier alone or in combinations. These molecules induce antitumor activity, cause tumor volume and size reduction, induce tumor necrosis and/or lysis, reduce pain due to cancer, induce reduction of autoimmune activity in autoimmune-mediated disease, reduce inflammatory processes and possess antiviral activity.

The mechanisms of action may be singular or multiple involving physiological, pathophysiological and immunological pathways. There may be effects of activating and/or stimulating and/or blocking specialized pathways and/or specialized receptor sites. There is a positive effect on the hemopoietic system. There appears to be effects on cell product secretion of many forms. These effects are beyond that of buffering capacity as evidenced by the effect on disease processes.

There may be further effects at the ionic level as well as distinct effects on membrane stability and permeability. Membrane stabilization may play an important role in causing abnormal cell division and abnormal cell function to normalize, either by external physiogenic factors or internal cellular functions, or both. In any event, this first description of the unique abilities of HEPES as a zwitterionic molecule and the effect upon disease processes is submitted.

The present invention relates to methods and compositions for inducing antitumor activity, tumor volume reduction, reduction of pain in cancer patients, induction of anti-flammatory response in autoimmune-mediated disease, reduction of the activity and progression of immunologically-mediated diseases, induction of the regression of tumor growth, induction of the regression of autoimmune activity in immunologically-mediated disease and antiviral effects. The invention shows a unique capability for inducing certain biochemical, physiological and immunological responses that cause lysis and/or necrosis of tumors and slowing the progression of diseases, including cancer, autoimmune disease and diseases caused by viral infection. In particular, the use of HEPES (N-2 Hydroxyethylpiperazine-N'-2 Ethane Sulfonic Acid), a zwitterionic molecule used generally as a buffer in salts or cell cultures, has demonstrated effects that are antitumorgenic, analgesic, anti-flammatory, reduction and/or progression of autoimmune diseases, and antiviral activity when used in certain compositions, alone or in conjunction with cell cultures. Additionally, HEPES appears to have an effect on cell culture immunological characteristics that are unique and not directly related to its buffering capability.

The present invention provides an effective treatment that is relatively non-toxic and safe. Its individual uniqueness is shown in many ways. For years, HEPES, a zwitterionic molecule, has been used as a buffer in mammalian cell cultures. It was not believed to have any specialized effects on cells. Certainly, it has not been viewed as an independent agent to treat cancer, cancer pain, autoimmune disease or certain infectious states. It is now shown that HEPES ($C_5H_{18}N_2O_4S$) (N-2 Hydroxyethylpiperazine-N'-2 Ethane Sulfonic Acid) and its homologs and analogs can, in certain preparations, have antitumorgenic effects on tumor growth, volume reduction, tumor activity and cancer pain. It also has an effect on reducing or reversing certain autoimmune diseases. Additionally, it appears to have antiviral effects. HEPES has been used as a buffer in cell culture technology. The invention became apparent when use of HEPES and human serum without cell culture was given as a control to patients who were intended to receive certain cell culture supernatants for experimental treatment of cancer, cancer pain and immune disease and viral infections.

All of the above effects can be shown when the HEPES is used alone or in combination with other biological compositions where the effect may be potentiated through specialized physiologic, biochemical and immunologic actions. It may potentiate production of known and unknown substances in mammalian cell cultures, the combinations of which may render more active compositions notwithstanding the individual effects of the substance. It further is noted that the effects described are clearly demonstrated outside of cell culture technology. Thus, HEPES is an immunological activator by itself. This would categorize HEPES as a true biological response modifier (BRM).

The present invention provides a method of preparing zwitterionic compositions for administration to a subject and the use of same compositions for the treatment of cancer, cancer pain, autoimmune diseases and infectious diseases.

The compositions used for administration comprise:

a) preparing certain concentrations of HEPES in solutions alone and/or with amino acids and/or L-glutamine and/or with bicarbonate;

b) preparing certain concentrations of HEPES in solutions with amino acids and/or L-glutamine and/or bicarbonate and/or human serum; and c) preparing certain concentrations of HEPES in solutions with amino acids and/or L-glutamine and/or bicarbonate and/or human serum and combines same with mammalian cell cultures, whether same cells in culture are transformed or not transformed, and using the supernatant and/or fractions of the supernatant alone or in combination to potentiate cellular production of immunological substances that are effective in working as biological response modifiers alone or in combination with zwitterionic compounds.

Also provided is a single or composition biological response modifier produced by the above methods.

The invention also provides a method of activating the immune system of a subject, comprising the above compositions when administered in an amount of the claimed compositions such that the immune system is activated. "Activating" can include activating, for example, a stimulator or blocker of immune activity.

Further provided is a method of increasing $CD_2$, $CD_3$, $CD_8$, and $CD_{20}$ counts and increases in stem cell production in subjects who are healthy or immunosuppressed comprising administration of HEPES, a zwitterionic molecule, in compositions as described that effect increases in certain hemopoietic mechanisms.

Also provided is a method of reducing tumor size and/or volume comprising administrating to the subject a composition containing HEPES, a zwitterionic molecule, in a tumor-reducing amount, compositions such that tumor size and/or tumor volume is reduced. Further, that the induction of tumor lysis and/or necrosis occurs due to the biological response modifier effect of HEPES as a zwitterionic compound.

The present invention provides a method of treating autoimmune diseases in a subject, comprising administering to the subject an amount of the compositions containing HEPES, a zwitterionic molecule, such that the progression of the autoimmune disease is slowed and/or reversed, the effect of which is due to HEPES as a biological response modifier.

Also provided are methods of treating pain due to inflammation and/or tumor activity and/or autoimmune disease activity comprised of administering an amount and certain compositions of HEPES, a zwitterionic molecule, to the subject.

Additionally provided are methods of treating viral infections in a subject comprising of administering an amount of HEPES compositions resulting in a decrease of viral activity.

Also provided are methods of treating immunosuppressed and/or immunodepressed subjects whose pathophysiological state may have been induced by drugs, toxins, radiation or environmental factors, by administering an amount of HEPES alone or by compositions.

The present invention provides methods of preparing solutions containing HEPES as: a) the active ingredient in solutions with HEPES and/or amino acids and/or L-glutamine and/or bicarbonate; b) the active and/or activating agent in solutions containing HEPES and/or amino acids and/or L-glutamine and/or bicarbonate and/or mammalian (human) serum; and c) HEPES and/or amino acids and/or L-glutamine and/or bicarbonate and/or human serum and/or human (mammalian) serum in cell culture. Cells used in cell culture preparations were human B lymphoid cells from a healthy donor. The cells had been transformed or activated by prior exposure to Epstein-Barr virus (EBV) which is confirmed by the presence of Epstein-Barr virus nucleic antigen (EBNA). Approximately sixty percent (60%) of the human population is Epstein-Barr virus nucleic antigen positive. There are other methods for cell activation such as endotoxin stimulation and protein activation stimulation (PAS) techniques, which are known to those of skill in the art. Further, the cells used are IgM secreting, and this is not considered a limiting factor The preparations containing HEPES in cell culture may be further combined by the presence of HEPES in terms of immunologically activating and/or stimulating and/or blocking effects of other cell secreted substances. The effects on cancer, cancer pain, autoimmune diseases and viral infections may be increased further by HEPES. It may be that the action of HEPES as a biological response modifier may be enhanced by the presence of certain substances secreted by cells in culture and/or HEPES or the substances may have synergism in activity and/or certain immunological pathways are activated, stimulated or blocked when HEPES is added to cell cultures due to one or more immunophysiological pathway actions. It is further acknowledged that additional and/or the same mechanisms are present when HEPES is combined with human serum. The serum may contain certain immunologically active substances that when combined with HEPES are potentiated and/or certain substances when combined with HEPES cause activation and/or stimulation and/or blocking of specialized pathways.

Additionally, HEPES, a biological response modifier, used alone or in various compositions, or other zwitterionic molecules, has shown effectiveness by positive indicators, such as, for example, tumor lysis and/or necrosis; decrease in the number and/or distribution of lesions; decrease in tumor size and/or volume; decrease in tumor markers; decrease in pain and/or analgesic usage; increase in immunological and hemopoietic markers; decrease in inflammation and markers associated with inflammatory processes; decrease in total viral loads; and decreases in auto antibody production in immune-mediated disease.

The present invention provides a method for activating or enhancing the immune system by stimulating and/or blocking and/or other immunophysiologic pathway effects consistent with a BRM, comprising administering to a subject an amount of HEPES in the compositions set forth. Indicators consist of increases in stem cell production, $CD_2$, $CD_3$, $CD_8$ and/or $CD_{20}$ counts. Other markers may include decreased antibody titers, rheumatoid factor (RF), antinuclear antibody (ANA) and anti-acetylcholine antibody. Positive changes in certain immunological cell secreted substances include, but are not limited to, cytokines, chemokines, kinases, immunoglobulins and other known biological response modifiers. Improvement is noted in subjects with rheumatoid arthritis and myasthenia gravis. Hemopoietic indicators show positive responses for immunosuppressed and immunodepressed states due to drugs, chemotherapy, radiation, toxins and/or environmental effects. Further positive hemopoietic indicators related to virally induced, immunosuppressed states in addition to cluster determinants and stem cells include P-24 antigen and beta-microglobulin levels. This invention contemplates all of the above embodiments and continues.

The invention further demonstrates that HEPES, a zwitterionic molecule, is shown to be a biological response modifier when HEPES, or other zwitterionic compositions, is used, alone or in combination, and administered to the subject, and results in tumor size and/or volume reduction and tumor lysis and/or necrosis. Tumor size, volume and necrosis can be detected and monitored by methods utilizing computerized axial tomography (CAT) and/or nuclear magnetic resonance imaging (MRI) and/or nuclear medicine scans, as known to those of skill in the art. Any tumor that is reduced or necrosed by this method utilizing HEPES or other zwitterionic molecules in the described compositions can be treated by this method, for example, tumors of ectodermal, mesodermal and endodermal origin, such as tumors associated with non-Hodgkins lymphoma; adenocarcinomas, mesothelioma, squamous cell carcinoma; embryonic testicular carcinoma; breast carcinoma; prostate carcinoma; ovarian carcinoma; gall bladder carcinoma, including signet cell type; cholangitic carcinoma; esophageal carcinoma; malignant melanoma; lung carcinoma; hepatoma; multiple myeloma; Kaposi's sarcoma; seminoma; brain tumor, including astrocytoma and glioblastoma, hepatoma, among many others, and further, that the tumor may be primary or metastatic as exemplified by the examples.

Also provided by the invention is a method of treating autoimmune diseases in a subject, comprising administering to the subject an amount of HEPES alone or other zwitterionic molecules in the described compositions such that the progression of the autoimmune pathology and/or pathophysiology of the disease is slowed, stopped or reversed. For example, the method can halt wasting, lower antibody titers, increase appetite, improve sleep and increase energy. The preferred method of composition utilizing HEPES alone or other zwitterionic molecules, alone or in compositions as previously described. Any autoimmune disease that responds favorably to this method, as can be tested, as taught herein, can be treated by this method, such as acquired immunodeficiency syndrome (AIDS); rheumatoid arthritis; myasthenia gravis; psoriasis; glomerulonephritis; thyroiditis; systemic lupus erythromatosis; multiple sclerosis; amyotrophic lateral sclerosis (AML); diabetes; aphthous stomatitis; lichen planus and chronic fatigue syndrome.

The present invention also provides a method of reducing a lesion caused by a virus in a subject, comprising administering an amount of HEPES alone or other zwitterionic molecules in the described compositions, such that the lesion is reduced. Preferred methods of composition are as previously described. Lesion progression and involvement can be monitored by standard methods known to those of skill in the art, for example, blood tests, antibody titers, measurement of lesions, as well as other evaluation techniques known to those of ordinary skill in the art. Lesions produced or induced by any virus that are reduced by this method are included in this invention; as can be tested by the methods herein, for example, Kaposi's sarcoma; herpes simplex; herpes zoster; and genital herpes.

The invention further provides a method of reducing the intensity and duration of a viral infection in a subject comprising administering to the subject an amount of HEPES or other zwitterionic molecules in the described compositions, such that the intensity and duration of the viral infection are reduced. The preferred method of treatment utilizes the methods of compositions previously described. The method can be utilized for any viral infection, the intensity and duration of which is reduced by the administration of a composition of the present invention, by the claimed method, as can be tested by the methods herein. Such viral infections are exemplified by the examples and can include, for example, infection by influenza viruses; rotavirus; adeno viruses; herpes viruses; immunodeficiency viruses and coxsackie viruses.

Further provided by this invention is a method of reducing pain and/or inflammation in a subject, comprising administering to the subject an amount of HEPES alone or other zwitterionic molecules in the described compositions, such that pain and/or inflammation are thereby reduced. A preferred method of treatment utilizes the methods of compositions as previously described. Pain remission can include remission of pain from a decrease in tumor size and/or volume, or in space-occupying lesions, thus decreasing organ pressure and compression of anatomical structures (i.e. nerves, vessels and other organs), as well as remission of pain not associated with a decrease in tumor size or volume or capsular stretching or a decrease in lesions, such as pain in bones and other pain that occurs before a significant decrease in tumor size or volume or lesion occurs. Such pain reduction may also be due to remission or reduction of inflammatory processes as in rheumatoid arthritis or other inflammatory and/or autoimmune diseases. Pain remission may also be due to changes in other physiologic, pathophysiologic and immune pathophysiologic improvement, such as; changes in production of endorphins and similar biochemicals; changes in nervous system activity and changes in ionic conditions and/or membrane permeability and/or membrane stability of a cellular or physiologic pathway levels.

A method of reducing effects of mental depression in a subject is also provided comprising administering to the subject an amount of HEPES alone or other zwitterionic molecules in the described compositions, such that the effects of mental depression are reduced. A preferred method of treatment utilizes the methods of compositions as previously described. Effects that are within this invention are those that can be reduced by this method, as can be tested by the methods taught herein and by standard protocols for measuring such effects. Examples of effects which can be reduced by this method include insomnia, weight loss, sadness/melancholy, clinical depression and feelings of isolation. Some results from this method include increased appetite, sense of well being, calmness, mood elevation and improved quality of sleep.

Also provided is a method of treating cancer in a subject comprising administering an amount of HEPES alone or other zwitterionic molecules in the described compositions, such that the progression of cancer is slowed, stopped or reversed. A preferred method of treatment utilizes the methods of compositions as previously described. Cancers included in this method are those which are reduced by this method as can be tested given the teachings herein. Some examples of such cancers include breast cancer; prostate cancer; non-Hodgkins lymphoma; cholangitic cancer (including signet cell type); glioblastoma; and others as previously stated. The cancers may be primary or metastatic. They include all cancers of ectodermal, mesodermal and endodermal origin.

Further provided herein is a method of treating hepatitis in a subject comprising administering to the subject an amount of HEPES alone or other zwitterionic molecules in the described compositions, such that the pathologic and pathophysiologic activity of hepatitis is reduced. Such pathologic and pathophysiologic activities that are reduced by this method include, for example, elevated bilirubin levels; and hepato-spleno-megaly. A preferred method of the treatment utilizes the methods of composition previously described. By "hepatitis", it is meant to include, for example, hepatitis A, hepatitis B, hepatitis C (formerly non-A, non-B) and alcoholic hepatitis.

Also provided herein is a method of reducing side effects of chemotherapy and radiation therapy in a subject comprising administering to the subject an amount of HEPES alone or other zwitterionic molecules in the described compositions, such that the side effects of chemotherapy and radiation therapy are reduced. A preferred method of treatment utilizes the compositions previously described. Side effects which can be reduced include nausea, vomiting and hair loss.

The present invention also provides a method of detecting infection in a subject comprising administering HEPES alone or other zwitterionic molecules in the described compositions to the subject and monitoring development at a reaction, such as fever, chills, diaphoresis and/or rigor by the subject, such development indicating presence of infection in the subject. A rapid search for infection can be accomplished whether such infection is clinical or sub-clinical with the etiology being bacterial, fungal or viral. It is further contemplated that the reactions of fever, chills and rigor may be immunologically mediated and therefore in vitro testing for immunological substances using controls against the subjects blood and/or cells would be developed. This may include measurement of cytokines (possibly IL-1 or others), chemokines, kinases and other cell-secreted products.

Further provided herein is a method for treating Alzheimer's disease in a subject comprising administering to the subject an amount of HEPES alone or other zwitterionic molecules in the described compositions, such that the pathologic and/or pathophysiologic activities are slowed and/or reversed. Such pathologic or pathophysiologic activities that are slowed or reversed by this method include, for example, improved memory, improved coordination, decreased agitation and improved quality of life. A preferred method of the treatment utilizes methods of composition previously described.

The compositions may be administered parenterally; e.g. intravenously, intramuscularly; subcutaneously, and the like. It is contemplated that oral preparation will be tried. The exact amount of a composition required will vary from subject to subject, depending upon species, age, weight, general condition of the subject, the severity of the disease that is being treated, the mode of administration used and the like. Thus, it is not possible to state an exact amount. Generally, dosages of 300 mg in compositions described may be given intravenously daily. Dosages of 25 mg intravenously daily have been given with responses noted in some diseases. Dosages of 1500 mg intravenously daily have been given with responses noted in some diseases. There have been complaints of headache and fatigue in a few subjects at higher dosages (<10%). Toxicity studies are contemplated as well as minimal dose response levels for each disease. Dosage may vary from less than 0.1 mg to greater than 5 grams daily intravenously. It is not possible at this time to state oral dosages until studies are completed. Length of therapy is yet to be determined.

Depending upon the intended mode of administration, the compositions can be in pharmaceutical compositions in solid, semi-solid or liquid forms. The total effect of a biological response modifier depends upon many variables, including compositions which as described may have increased effects depending upon type of disease and pharmaceutical form. As described, compositions may have HEPES alone or other zwitterionic molecules alone or with mammalian serum or with supernatants or supernatant fractions, filtered or unfiltered, each having different bioactivity and biological response modifier capability on different disorders and diseases. In addition, depending upon mode of administration and the composition, the composition may be provided with pharmaceutically acceptable carriers and, in addition, may include any other medicinal agents, pharmaceutical agents, carriers, adjuvants, diluents, etc. that do not interfere with the activity of the composition, for example, saline solutions. By "pharmaceutically acceptable" is meant that a material that is not biologically or otherwise undesirable, i.e., without causing any undesirable biological effects or interacting in a deleterious manner with any of the components of the pharmaceutical composition in which it is contained.

The present invention is more particularly described in the following examples which are intended as illustrative only, since numerous modifications and variations therein will be apparent to those skilled in the art.

The zwitterionic molecular compounds useful in treatment many vary in effective, therapeutic concentrations depending upon the disease and condition of the mammal.

However, generally effective, therapeutic concentrations range from about a low of 0.1, e.g. 10 mg to 50 mg, to as high as 500 mg, or more like 1500 mg, for example and preferably, about 25 mg to 500 mg, alone or in combination with other representative pharmaceutical carrier compounds, like saline solution, bulking agents, stabilizers, inert ingredients, or other active ingredients, such as amino acid compounds, like, but not limited to, carbohydrate amines, like L-glutamine, in varying amounts, for example, of 1 mg to 100 mg. Other amino acids for use with HEPES include L-alanine; L-Araline HCl; L-Asparagine-$H_2O$; L-Aspartic Acid; L-Cystine-2HCl; L-Glutamic Acid; Glycine; L-Hstidine-HCl-$H_2O$; L-Isoleucine; L-Leucine; L-Lysine-HCl; L-Methionine; L-Phenylalanine; L-Proline; L-Serine; L-Tryptophan; L-Tyrosine-2Na; L-Valine; as well as vitamins including d-Biotin; D-Ca Pantothenate; Choline Chloride; Folic Acid; i-Inositol; Nicotinamide; Pyridoxine-HCl; Riboflavin; Thiamine-HCl and Vitamin $B_{12}$. Typically, the zwitterion molecular compositions are employed in sterile liquid form in saline solutions, such as in syringes or intravenous containers or bags, and contain a buffer agent, such as phosphate or bicarbonate or other buffers, like sodium and potassium, in saline solution.

Piperazine zwitterion compounds of the invention include zwitterion piperazine compounds with an hydroxyl and a sulfonic acid group like those compounds having the structural formula:

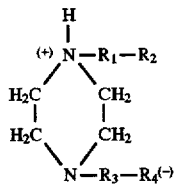

wherein $R_1$ is an N-linking group, like an alkylidene group, such as $C_1$-$C_6$ alkylidene; $R_2$ is an hydroxyl or amine; $R_3$ is an N-linking group, like an alkylidene, such as $C_1$-$C_6$; and $R_4$ is an acid or substituted acid, like citrate, adipic, carboxylic (COOH); phosphoric ($PO_4OH$) or sulfonic ($SO_2OH$) acid and the salts of the zwitterion compound.

The zwitterion molecular compositions also useful contain human serum in effective and carrier amounts, like A, O, B and particularly, AB human serum certified to be negative for bacteria, mycoplasma, hepatitis, TB, HTLVI AND II, and other infectious agents or components.

Some representative compositions prepared and useful in the invention are:

| Compositions of Zwitterionic Molecular Compounds | |
|---|---|
| Type A | 100–300 mg HEPES ultra pure |
| | 1.6 cc L-glutamine |
| | Amino acids |
| | Bicarbonate buffer |
| Type B | 100–300 HEPES ultra pure |
| | 1.6 cc L-glutamine |
| | .8 cc human AB serum |
| | Amino acids |
| | Bicarbonate buffer |
| Type C | 100–300 mg HEPES |
| | 1.6 cc L-glutamine |
| | .8 cc–1.0 cc human AB serum |

Normal administration was in 50 cc normal saline (0.9% saline solution) given intravenously over 15–30 minutes.

DESCRIPTION OF THE EMBODIMENTS

The present invention may be understood more readily by reference to the following detailed description of specific embodiments and the examples included therein.

EXAMPLES

Subject One

A sixty-five year old white male with a five year history of prostate cancer. The patient had multiple metastases to bone sites. His pain was intense. He was receiving 400 mg of morphine, 6 Dilaudid tablets and 3 Darvocet-N tablets daily.

The patient was given a composition of 300 mg HEPES, 1 cc human serum, 1 ml L-glutamine with amino acids and bicarbonate combined with a human cell culture supernatant (intravenously with normal saline) daily for one month. At the end of the month, the patient had significant pain reduction. He required no narcotics at all and took occasional non-steroidal anti-inflammatory medication for occasional discomfort. His Prostatic Specific Antigen (PSA) had declined to 50% from baseline.

Subject Two

A sixty-two year old Korean male with a two year history of pancreatic carcinoma with documented extension. The patient had severe pain with duct obstruction and was moribund. He was unable to eat or take fluids orally. He was receiving 35 mg of Demerol per hour intravenously.

The patient was given 100 mg HEPES, 0.8 cc human serum, 1.6 cc L-glutamine with amino acids in normal saline (50 cc) twice daily for two weeks (no cell culture). At the end of five days, his IV Demerol was reduced to 15 mg per hour. After seven days, he was receiving 5 mg per hour. He was able to take soft solids and fluids. He could stand unassisted. After two weeks, he required only oral Demerol and was comfortable and functional. His tumor marker CA 19-9 had decreased more than 25% from baseline.

Subject Three

A sixty-five year old white male with signet cell carcinoma of the gall bladder with extensive retroperitoneal involvement. He was unable to eat. His carcinogenic embryonic antigen (CEA) level was 1300. His liver functions showed an alkaline phosphatase >450 mg/ml, SGOT >100, SGPT>60, LDH>200. He was taking morphine for pain.

The patient was given 300 mg HEPES, 0.8 cc human serum, 1.6 cc L-glutamine with amino acids (no culture supernatant) intravenously in 50 cc normal saline daily for four weeks. After four weeks, his CEA level fell to 600. His liver function SGOT, SGPT and LDH were normal. Alkaline phosphatase was <200. He was essentially pain free. He could take liquids and soft solids.

Subject Four

A fifty-eight year old female with a greater than a five year history of severe rheumatoid arthritis. She had severe pain. She had failed to respond to gold and methotrexate therapy.

She was given 300 mg HEPES, 1.6 cc L-glutamine (no human serum, no cell culture) in 50 cc normal saline for two weeks. After two weeks, she had no significant pain. Non-steroidal anti-inflammatories (NSAIDs) was the only medication needed for her to be mobile and comfortable. Her erythrocyte sedimentation rate (ESR) was 50% of baseline. Rheumatoid factor and ANA were decreased.

Subject Five

A seventy-two year old male with a ten year history of recurrent Kaposi's sarcoma. All previously removed. No evidence of internal malignancy. Patient had a recurrence on the right foot.

Patient was given 300 mg HEPES, 1.6 cc L-glutamine, 0.8 cc human serum with amino acids in 50 cc normal saline IV three times a week. He also received 30 mg HEPES, 0.1 cc human serum, 0.2 cc L-glutamine with amino acids as an intralesional injections three times a week (total 5 cc volume). After four weeks, the lesions disappeared and have not returned. Kaposi's sarcoma is a virally-mediated tumor.

What is claimed is:

1. A method for the treatment in a mammal of tumorous cancers and autoimmune diseases, which method consists essentially of: administering to the mammal with the disease a therapeutic effective amount of a biological response modifier composition having as its active ingredient a zwitterion compound and its pharmaceutically acceptable salts having the structural formula:

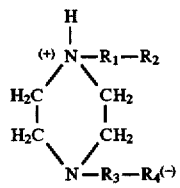

wherein $R_1$ and $R_3$ are $C_1$–$C_6$ alkylidene radicals; $R_2$ is a hydroxyl or amine radical; and $R_4$ is a carboxylic, phosphoric or sulfonic acid radical.

2. The method of claim 1 wherein said compound is N-(2-hydroxyethyl)piperazine-N'-2-ethanesulfonic acid.

3. The method of claim 1 wherein a therapeutic effective amount of the said compound ranges from about 10 mg to –1500 mg.

4. The method of claim 1 which includes administering the composition intravenously to the mammal.

5. The method of claim 1 which includes administering the composition orally to the mammal.

6. The method of claim 1 wherein the composition includes human serum.

7. The method of claim 6 wherein the composition comprises a sterile liquid buffered saline composition which includes human serum.

8. The method of claim 1 wherein the composition includes human cell culture supernatant.

9. The method of claim 1 wherein the composition includes an amino acid.

10. The method of claim 9 wherein the composition includes about 1 mg to 100 mg of an amino acid.

11. The method of claim 1 which includes the method of treating diseases of the mammal selected from the group consisting of: prostate cancer; pancreatic carcinoma; signet cell carcinoma; rheumatoid arthritis and Kaposi's sarcoma.

12. The method of claim 1 wherein the composition includes human serum, an amino acid, and human cell culture supernatant, and the zwitterion compound comprises from about 10 mg to 500 mg.

13. A method for the treatment in a mammal of tumorous cancers and arthritic diseases, which method consists essentially of administering to the mammal with the disease a therapeutic effective amount of a biological response modifier composition which comprises as the active ingredient about 10 mg to 1500 mg of a N-(2-hydroxyethyl)piperazine-N'-2-ethanesulfonic acid and its pharmaceutically acceptable salts.

14. The method of claim 13 wherein the composition includes an amino acid.

* * * * *